US007960135B2

(12) United States Patent
Chenn (10) Patent No.: US 7,960,135 B2
(45) Date of Patent: Jun. 14, 2011

(54) COMPOSITIONS AND METHODS FOR CELL CHARACTERIZATION (75) Inventor: Anjen Chenn, Evanston, IL (US)

(73) Assignee: Northwestern University, Evanston, IL (US)

(*) Notice: Subject to any disclaimer, the term of this patent is extended or adjusted under 35 U.S.C. 154(b) by 41 days.

(21) Appl. No.: 11/725,778

(22) Filed: Mar. 20, 2007

(65) Prior Publication Data
US 2007/0298450 A1 Dec. 27, 2007

Related U.S. Application Data (60) Provisional application No. 60/784,006, filed on Mar. 20, 2006.

(51) Int. Cl.
C12Q 1/02 (2006.01)
G01N 21/00 (2006.01)
G01N 21/76 (2006.01)
(52) U.S. Cl. .......................... 435/29; 436/164; 436/172
(58) Field of Classification Search .................... None
See application file for complete search history.

(56) References Cited

U.S. PATENT DOCUMENTS
2003/0113709 A1* 6/2003 Alivisatos et al. ............... 435/4

OTHER PUBLICATIONS

Steinkamp et al. Phagocytosis: Flow Cytometric Quantitation With Fluorescent Microspheres; Science, vol. 215 (1982) pp. 64-66.*
Windler-Hart et al. A Cell Behavior Screen: Identification, Sorting and Enrichment of Cells Based on Motility; BMC Cell Biology, vol. 6, No. 14 (2005) pp. 1-9.*
Parak et al. Cell Motility and Metastatic Potential Studies Based Upon Quantum Dot Imaging of Phagokinetic Tracks; Advanced Materials, vol. 14, No. 12 (2002) pp. 882-885.*
Pellegrino et al. Quantum Dot-Based Cell Motility Assay; Differentiation, vol. 71 (2003) pp. 542-548.*
Flow Cytometry Signals (2005) downloaded from http://med.umich.edu/flowcytometry/InitialTraining/lessons/lesson1/index.htm on Jan. 15, 2009.*
Yamaya et al. Cytoplasmic Motility Reflects Phagocytic Activity in Alveolar Macrophages From Dog Lungs; Respiration Physiology, vol. 101 (1995) pp. 199-205.*
Albrecht-Buehler "The phagokinetic tracks of 3T3 cells" 1977 Cell 11:395-404.
Boyden, "The Chemotactic Effect of Mixtures of Antibody and Antigen on Polymophonuclear" Leucocytes J Exp Med 1962, 115:453-466.
Clark et al., "Genomic analysis of metastasis reveals an essential role for RhoC" 2000 Nature 406:532-535.

Flow Cytometry Signals 2005 downloaded from http://med.umich.edu/flowcytometry/InitialTraining/lessons/lesson1.htm on Jan. 15, 2009, (anonymous).
Katz et al., "Fluorescent latex microspheres as a retrograde neuronal marker for in vivo and in vitro studies of visual cortex" 1984 Nature 310:498-500.
Klein et al., "Combined transcriptome and genome analysis of single micrometastatic cells" 2002 Nat Biotechnol 20:387-392.
Liotta and Kohn, "The microenvironment of the tumour-host interface" 2001 Nature 411:375-379.
Parak et al., "Cell Motility and Metastatic Potential Studies Based Upon Quantum Dot Imaging of Phagokinetic Tracks" 2002 Advanced Materials vol. 14 No. 12 pp. 882-885.
Pellegrino et al., "Quantum Dot-Based Cell Motility Assay" 2003 Differentiation vol. 71 pp. 542-548.
Perou et al., "Molecular Portraits of Human Breast Tumours" Nature 2000, 406:747-752.
Rembaum and Dreyer, "Immunomicrospheres: reagents for cell labeling and separation" 1980 Science 208:364-368.
Ridley et al., "Cell migration: integrating signals from front to back" Science 2003, 302:1704-1709.
Scott et al., "Improved method for the production of gold colloid monolayers for use in the phagokinetic track assay for cell motility" 2000 Anal Biochem 287: 343-344.
Sheen et al., "Mutations in ARFGEF2 implicate vesicle trafficking in neural progenitor proliferation and migration in the human cerebral cortex" 2004 Nat Genet 36:69-76.
Steinkamp et al., "Phagocytosis: Flow Cytometric Quantitation With Fluorescent Microspheres" 1982 Science 215:64-66.
Wadsworth, "Microinjected carboxylated beads move predominantly poleward in sea urchin eggs" 1987 Cell Motil Cytoskeleton 8:293-301.
Wang et al., "Gene expression analysis on small numbers of invasive cells collected by chemotaxis from primary mammary tumors of the mouse" BMC Biotechnol 2003, 3:134, 18, 19.
Wang et al., "Single Cell Behavior in Metastatic Primary Mammary Tumors Correlated with Gene Expression Patterns Revealed by Molecular Profiling1,2"Cancer Res 2002, 62: 6278-6288.
Windler-Hart et al., "A Cell Behavior Screen: Identification, Sorting and Enrichment of Cells Based on Motility" 2005 BMC Cell Biology vol. 6 No. 14pp. 1-9.
Yamaya et al., "Cytoplasmic Motility Reflects Phagocytic Activity in Alveolar Macrophages From Dog Lungs" 1995 Respiration Physiology vol. 101 pp. 199-205.
Zetter, "Migration of capillary endothelial cells is stimulated by tumour-derived factors" 1980 Nature 285: 41-43.
Zlokarnik et al., "Quantitation of transcription and clonal selection of single living cells with beta-lactamase as reporter" 1998 Science 279:84-88.

* cited by examiner

Primary Examiner — Rebecca E. Prouty
Assistant Examiner — Paul C. Martin
(74) Attorney, Agent, or Firm — Casimir Jones, S.C.

(57) ABSTRACT

The present invention relates to compositions and methods for identification, sorting and enrichment of cells. In particular, the present invention provides compositions and methods for quantitation of cell motility by measurement of individual cell motility, and rapid isolation of cell populations, using fluorescent signal within single cells. Such compositions and methods find use in clinical, therapeutic and research settings.

9 Claims, 4 Drawing Sheets

COMPOSITIONS AND METHODS FOR CELL CHARACTERIZATION

The present invention claims priority to U.S. Provisional Patent Application No. 60/784,006, filed Mar. 20, 2006, hereby incorporated by reference in its entirety.

FIELD OF THE INVENTION

The present invention relates to compositions and methods for identification, sorting and enrichment of cells. In particular, the present invention provides compositions and methods for quantitation of cell motility by measurement of individual cell motility, and rapid isolation of cell populations, using fluorescent signal within single cells. Such compositions and methods find use in clinical, therapeutic and research settings.

BACKGROUND OF THE INVENTION

Identifying and isolating cells with specific behavioral characteristics (e.g., motility) will facilitate the understanding of the molecular basis regulating these behaviors. Although many approaches exist to characterize cell motility, retrieving cells of specific motility following analysis remains a challenge.

SUMMARY OF THE INVENTION

The present invention relates to compositions and methods for identification, sorting and enrichment of cells. In particular, the present invention provides compositions and methods for quantitation of cell motility by measurement of individual cell motility, and rapid isolation of cell populations, using fluorescent signal within single cells. Such compositions and methods find use in clinical, therapeutic and research settings.

Accordingly, in some embodiments, the present invention provides a method of analyzing cell motility comprising: providing a cell; and a substrate covered with fluorescent microspheres; contacting the cell with the substrate; measuring the amount of fluorescence cleared by the cell; and correlating the area cleared with the motility of the cell. In some embodiments, the method is used to quantitate the motility of a single cell. In some embodiments, the method is used to quantitate the motility of a population of cells. In some embodiments, the method is used to sort cells. In some embodiments, the method is used to enrich a population of cells. In some embodiments, the same cell is placed through the assay two or more times. In some embodiments, the cell generates a non-fluorescent track as the cells migrates. In some embodiments, the non-fluorescent track is generated by the cell moving and ingesting the microspheres. In some embodiments, the non-fluorescent track is quantified and correlated to the amount of movement of the cell. In some embodiments, the method permits recovery of the cell populations. In some embodiments, the method is used to identify factors that regulate motility. The present invention is not limited by the type of microspheres (e.g., comprising a detectable marker (e.g., fluorescent dye)) utilized. Indeed a variety of microspheres may be used including, but not limited to, various types of FLUOSPHERES and TRANSFLUO-SPHERES (e.g., available from INVITROGEN, Carlsbad, Calif.), polystyrene microspheres, carboxylate-modified microspheres, sufate microspheres, aldehyde-sulfate microspheres, and amine-modified microspheres. Furthermore, microspheres utilized may be of a homogenous (i.e., nearly all the same size) or heterogeneous (i.e., comprising a variety of sizes) population of microspheres ranging in size from about 0.02 µm in diameter to about 15 µm in diameter, although smaller and larger microspheres may find use in certain applications using the compositions and methods of the present invention. In some embodiments, the fluorescent microspheres are selected from the group consisting of polystyrene microspheres, carboxylate-modified microspheres, sufate microspheres, aldehyde-sulfate microspheres, and amine-modified microspheres.

The present invention also provides a method of enriching a population of cells comprising: providing: a plurality of cells; and a substrate covered with fluorescent microspheres; contacting the plurality of cells with the substrate; providing time for the cells to migrate on the substrate; and sorting the cells. In some embodiments, the cells are sorted based on fluorescence intensity. In some embodiments, the cells are sorted based on side scatter characteristics. In some embodiments, the fluorescence intensity is correlated with the motility of the cells. In some embodiments, the cells with a greater amount of fluorescence intensity compared to cells with a lower amount of fluorescent intensity is indicative of cells with greater motility. In some embodiments, the cells are cultured post sorting the cells (e.g., for research, clinical or therapeutic applications).

DESCRIPTION OF THE DRAWINGS

FIG. 1 shows the appearance of cells migrating on fluorescent microspheres. (A) F-actin, DNA, microspheres, and merged view indicate that cells clear non-fluorescent tracks in the dense particle field as they move. Bar, 100 µm. (B) Cell lines exhibit differences in motility reflected by the area of particles cleared, highlighted by comparing T98G and U118MG glioblastoma lines. Bar, 300 µm. (C) Cells transfected with expression vector for GFP can be visualized on a blue fluorescent microsphere field. The trails from both cells converge at a common origin, providing that the two cells arose from the division of a common progenitor and migrated away. Bar, 20 µm. (D) Confocal section of phalloidin-stained U118MG cell migrating on field of blue microspheres. Bar, 20 µm.

FIG. 2 shows characteristics of fluorescent phagokinetic assay. (A) Transwell cell motility assay. A greater number of U118MG cells (1.33 fold) transit through the filter compared with T98G. Graph depicts the mean number of cells that transit through the filter of 5 10× fields in 4 replicate wells/cell line (20 fields/cell line/experiment) from 3 independent experiments; p=0.0185). (B) Mean area of fluorescent particles cleared per cell reveals U118MG cell line exhibits greater intrinsic motility than T98G (2.29 fold greater area cleared/cell). Graph depicts the mean motility of cells, 100 cells/cell line measured for each experiment; p=0.0012. (C) Fluorescent phagokinetic assay reveals differences in motility of cell lines (primary mouse cerebral cortical astrocytes, T98G, U118MG) on different extracellular matrices (fibronectin (FN), type IV collagen, laminin). * indicates p<0.001 comparing motility of U118MG on FN vs. Collagen IV or FN vs. laminin. For all pairwise comparisons of U118MG on any substratum vs. either T98G or primary astrocytes, p<0.001. (D) Histogram of distribution of areas cleared by U118MG vs. T98G from a representative experiment on poly-D-lysine treated tissue culture plastic (no additional substratum). Results are expressed as means+/−SEM, and statistical significance was evaluated by Student's t-test (A, B) or one-way ANOVA followed by Newman-Keuls post-hoc test (C).

FIG. 3 shows the relationship of fluorescence and motility. After migration on fluorescent beads, single cell fluorescence of T98G (A) and U118MG cells (B) is linearly related to area of fluorescent microspheres cleared by the cell. Fluorescence intensity of individual migrating cells was obtained by tracing each cell outline and measuring total fluorescent signal. Area cleared by each cell was measured by outlining cleared area. Images were collected using a 10× phase objective, 0.3 NA, and Endow GFP filter cube, and captured with a 16 bit CCD camera (CASCADE 650, Roper Inc.).

FIG. 4 shows flow-cytometric sorting of cells based on motility. (A) Fluorescence distribution of U118MG resembles distribution of cell motility seen in phagokinetic motility assay (left). The y-axis represents the number of cells characterized in each bin; the x-axis represents cell fluorescence at 525 nm. An untransformed linear scale for fluorescence intensity is used. On a linear scale, the voltage measured (signal intensity) is directly proportional to the channel into which the event falls. A cell with a linear value of 100 is 10 times brighter than one in with a linear value of 10. Side-scatter and fluorescence characterization of U118MG after 20 hours of migration on fluorescent microspheres (middle). Cells were sorted using the gates drawn. Granularity (side scatter) reflects the quantity of ingested beads, and is directly related to cell fluorescence. 1023 channels are available to bin the signal from fluorescence, forward, and side scatter. Forward scatter (a measure of cell size) and side scatter (a measure of cell granularity) characterization of U118MG indicates that there is no relationship between cell size and bead internalization (right). (B) Cell size is not related to cell fluorescence. Forward scatter vs. fluorescent signal of analyzed cells show no relationship between cell size and fluorescence (left). (C) Flow characterization of sorted cells. A small sample of recovered cells were re-analyzed after sorting with gates shown in (A), and both gated populations (low and high fluorescence) show no relationship between cell size (forward scatter) and cell fluorescence. (D) Images of low fluorescence cells (left) and high fluorescence cells (right) 24 hours post sorting, plated onto tissue culture plastic treated with 50 µM poly-D-lysine. Bar=20 µm. (E) Cells retain differences in motility when reassayed after one, two, three, and five weeks post-sort (n>100 cells/cell line at each time point). Cell motility was assayed by measuring the area cleared/cell over 24 hours using the fluorescent phagokinetic assay. The overall mean fold difference between the two cell lines is 1.20, p=0.0230. The mean motility of the high motility cell line was significantly different than the low motility cell line at each time point measured (week 1, 1.23 fold difference, p=0.0106; week 2, 1.23 fold difference, p=0.0105; week 3, 1.17 fold difference, p=0.0195; week 5, 1.18 fold difference, p=0.0201). Results are expressed as means+/−SEM, and statistical significance was evaluated by Student's t-test at each time point.

DETAILED DESCRIPTION OF THE INVENTION

The present invention relates to compositions and methods for identification, sorting and enrichment of cells. In particular, the present invention provides compositions and methods for quantitation of cell motility by measurement of individual cell motility, and rapid isolation of cell populations, using fluorescent signal within single cells. Such compositions and methods find use in clinical, therapeutic and research settings.

Many developing tissues are comprised of morphologically indistinguishable cells. However, these cells are often heterogeneous with respect to gene and protein expression, as well as developmental potential. Differences that develop from initially clonal cancer cell populations underlie the emergence of cells resistant to initial therapeutic intervention, and the ability of certain cancers to spread may relate in part to the intrinsic motility of cancerous cells (See, e.g., Liotta and Kohn, Nature 2001, 411:375-379). Methods that facilitate the identification and isolation of cells exhibiting specific behaviors are needed, that in turn will lead to greater understanding of molecular mechanisms underlying cancer progression.

The identification of differences in gene and protein expression that contribute to carcinogenesis depends on the specific identification and isolation of abnormal cells. Although recent advances in tissue microdissection enables highly specific isolation of cells from tissue samples (See, e.g., Bonner et al., Science 1997, 278:1481, 1483), the ability to identify and isolate living cells based on specific behavioral characteristics may provide valuable insights that are not evident from static morphological analysis of tissue (See, e.g., Wang et al., Cancer Res 2002, 62:6278-6288; Wang et al., BMC Biotechnol 2003, 3:13).

Although several methods to examine cell motility exist, most characterize motility on a cell population basis, cannot distinguish heterogeneity within a population, and do not permit isolation of cells with specific motility. Variations of a classic chemotactic assay initially described by Boyden (See, e.g., Boyden, J Exp Med 1962, 115:453-466) have been effectively used to characterize the motility of a variety of cell populations. These assays typically monitor the movement of cells to the opposite side of a porous membrane onto which they are initially plated in high numbers. Typically, Boyden/transwell assays reveal differences in motility of the most motile fraction of the entire populations analyzed, because the vast majority of cells do not pass through the transwell membrane. Finally, although these assays have proven to be somewhat versatile, they require large starting numbers of cells, and isolation of cells possessing distinct motility remains a challenge.

It has been observed that cells moving on substrates coated with supra-colloidal gold particles generate a record of their movements by clearing the particles from their path (See, e.g., Albrecht-Buehler, Cell 1977, 11:395-404). This clearing of a particle-free trail by a combination of cell locomotion and phagocytosis, described as "phagokinetics," has been used to quantify the motility of a variety of cell types (See, e.g., Albrecht-Buehler, Cell 1977, 11:395-404; Scott et al., Anal Biochem 2000, 287:343-344; Zetter, Nature 1980, 285:41-43). Accordingly, in some embodiments, the present invention provides a method that enables quantitation of motility both by direct measurement of cleared area and by fluorescent signal intensity within single cells, and permits isolation of cells (e.g., based on their motility and/or amount of fluorescence present within the cells).

The utility of using fluorescence to sort motile cells depends in part on the close relationship of bead accumulation and motility, and a number of factors may potentially confound interpretation of the described approach. There was no toxicity or ill consequences from phagocytosis of beads observed using a motility assay of the present invention. Cell proliferation was unaffected, and cells plated on microspheres could be sorted, re-plated, expanded, and re-examined using the same assay multiple times. After several rounds of cell division, the beads were eventually diluted away, and the cells could be re-assayed again. Thus, the present invention provides an assay that can sort, re-plate, and expand cells in a repetitive manner (e.g., using the assay multiple times (e.g., to recover certain cell populations)).

If the accumulation of beads is affected by other factors in addition to motility, fluorescence may not reflect motility accurately. Although an understanding of the mechanism is not necessary to practice the present invention and the present invention is not limited to any particular mechanism of action, in some embodiments, bead ingestion is not affected by factors other than motility for a number of reasons: 1) the beads are adherent to the substrates and thus are not free to be ingested by cells without direct contact; 2) the tracks generated by migrating cells are continuous, bead-free paths, indicating that cells do not exhibit periods of migration without bead ingestion; 3) accumulation of fluorescent beads correlates directly with the degree of cell migration as recorded by cleared areas, as well as the quantity of beads cleared (See e.g., FIG. 4). Fluorescence of the cells was identical to the fluorescence of an equal area of uncleared microspheres adjacent to the cleared area (e.g., no evidence of differences by paired t-tests), providing that all of the beads that are cleared are ingested by the cell.

In some embodiments, there is a maximum quantity of beads that any given cell can ingest, and as the cell approaches this limit with sustained migration, the relationship of cell fluorescence and motility may diverge as fluorescence plateaus. However, in experiments conducted during development of the present invention, a plateau in fluorescence after 24 hours of migration was not observed, with a linear relationship maintained between fluorescence and motility (See, e.g., FIG. 4). Although an understanding of the mechanism is not necessary to practice the present invention and the present invention is not limited to any particular mechanism of action, in some embodiments, highly motile, slowly dividing (or non-dividing) cells might approach a limit to bead consumption, or cells may migrate differently upon the microsphere substrate than on uncoated substrates. Thus, in some embodiments, a lower concentration of beads are used, or the assay time is constrained, to address these issues.

Figure 1:
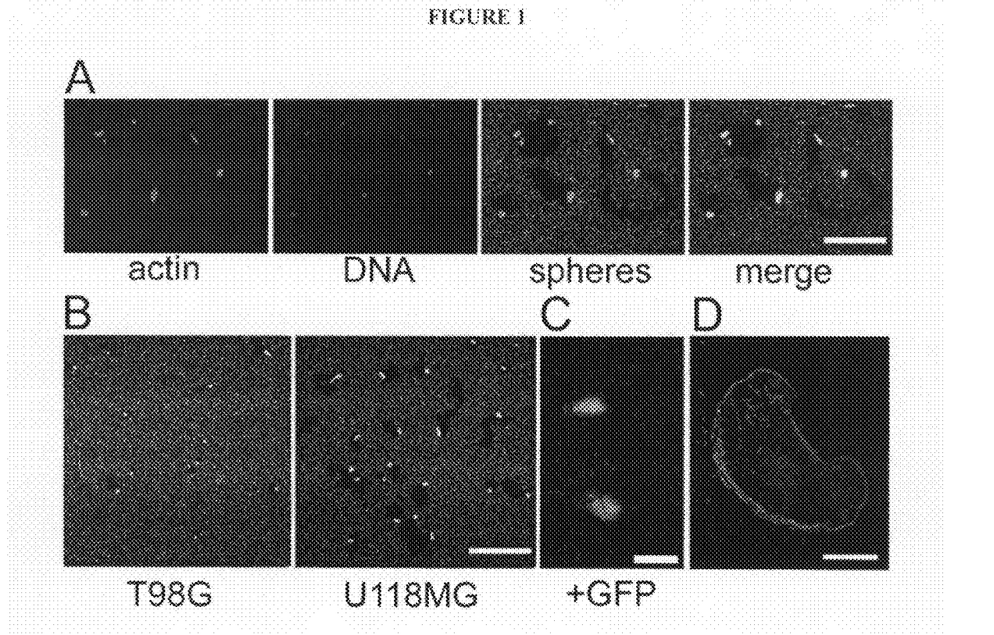

Existing methods to quantify motility such as transwell assays, wound healing assays, and cell outgrowth assays can be complicated by cell division, and investigators have resorted to including mitotic inhibitors in their assays. In contrast, cells that have divided in the fluorescent phagokinetic assay are easily identified by the cleared trail leading from the two cells (See example shown in FIG. 1C). As a consequence, the present invention provides the ability to easily measure the path areas of single cells to exclude cells that have divided in the period since plating. Although one approach typically used to quantify motility when utilizing the phagokinetic assay is to report a total area cleared, in some embodiments, reporting the area cleared per cell is more representative of cell motility than reporting total area cleared (e.g., as this quantity will not be confounded by cell division).

In some embodiments, a motility assay of the present invention can complement existing assays of cell motility. For example, in some embodiments, an assay of the present invention is especially useful when starting cell numbers are limiting, or when recovery of particular populations is desirable. Furthermore, in contrast to the commonly used transwell assay (e.g., that documents the movements of the highest motility cells in a population), an assay of the present invention, in some embodiments, characterizes an unselected sample of the population, and can therefore provide unbiased information about motility characteristics of the entire cell population.

Behavioral readouts are a most direct screen for molecular pathways that regulate the behavior of interest. Although traditionally, screens are thought of on an organism level, the present invention describes, in some embodiments, screening for differences in a specific cell behavior. In some embodiments, populations of cells can be selected by in vivo behaviors. For example, characterization of cells selected for the ability to metastasize revealed a number of genes involved with tumor cell invasion (See, e.g., Clark et al., Nature 2000, 406:532-535). As demonstrated herein, further resolution on a single cell basis can be valuable even in apparently homogeneous or clonal cell populations, as individual cells can exhibit wide variations in motility. Thus, to gain additional insight into the molecular mechanisms underlying differences in cell behavior, reporter assays for gene expression with single cell fidelity (See, e.g., Zlokarnik et al., Science 1998, 279:84-88), combined with genome-wide analysis of expressed genes (See, e.g., Perou et al., Nature 2000, 406: 747-752; Klein et al., Nat Biotechnol 2002, 20:387-392) may be used in combination with a motility assay of the present invention.

In some embodiments, the present invention provides compositions and methods to characterize differences in motility of a clonally-derived cell line. In some embodiments, further characterization can determine the molecular underpinnings that generate the differences in intrinsic cell motility. In some embodiments, a motility assay of the present invention permits characterization of heterogeneity that exists within the sorted populations. Although an understanding of the mechanism is not necessary to practice the present invention and the present invention is not limited to any particular mechanism of action, in some embodiments, characterization is made possible because a motility assay of the present invention enables 1) enrichment of populations by re-sorting previously enriched cell populations and 2) resolution of cell populations by sorting into single cells with subsequent characterization using a variety of approaches (See, e.g., Wang et al., BMC Biotechnol 2003, 3:134, 18, 19; Perou et al., Nature 2000, 406:747-752; Klein et al., Nat Biotechnol 2002, 20:387-392).

Thus, a phagokinetic motility assay (e.g., a fluorescent phagokinetic motility assay) of the present invention provides multiple advantages over existing assays of cell motility. First, the preparation of substrate is straightforward, comprising, in some embodiments, the application of fluorescent microspheres to a substrate, and allowing them to adhere. The present invention is not limited by the type of microsphere utilized. Indeed, any type of microsphere to which a marker (e.g., fluorescent molecule or dye, biotin, streptavidin) can be attached finds use in the present invention. Examples of microspheres include, but are not limited to, various types of FLUOSPHERES and TRANSFLUOSPHERES (e.g., available from INVITROGEN, Carlsbad, Calif.), polystyrene microspheres, carboxylate-modified microspheres, sufate microspheres, aldehyde-sulfate microspheres, and amine-modified microspheres. Furthermore, microspheres utilized may be of a homogenous (i.e., nearly all the same size) or heterogeneous (i.e., comprising a variety of sizes) population of microspheres ranging in size from about 0.02 µm in diameter to about 15 µm in diameter, although smaller and larger microspheres may find use in certain applications using the compositions and methods of the present invention.

Second, the assay is highly sensitive. For example, single cell characteristics, including the behavior of individual transfected cells, can be obtained in an unbiased fashion. Furthermore, because cell fluorescence is related to the area of fluorescent particles cleared, distinct subpopulations of cells can be sorted and enriched based on degree of motility. Thus, in some embodiments, an assay of the present invention is used to identify factors that regulate motility differences (e.g., even within clonal population of cells). In some embodiments, this approach is extended beyond two dimensions by creating three dimensional suspensions of fluorescent particles in solid matrices to also provide screens to identify additional parameters of motility and oncogenesis in vivo.

EXPERIMENTAL

The following examples are provided in order to demonstrate and further illustrate certain preferred embodiments and aspects of the present invention and are not to be construed as limiting the scope thereof.

Example 1

Materials and Methods

Transwell migration assay. Cell migration through transwell filters was analyzed as described (See, e.g., Sheen et al., Nat Genet 2004, 36:69-76), with minor modifications. Briefly, $1\times10^5$ T98G and U118MG cells were seeded on the top of transwell membranes treated with 50 µg/ml poly-D-lysine for 30 min (8 µm pore diameter; Becton Dickinson) in media (DMEM) with 20% fetal bovine serum in both upper and lower compartments and allowed to migrate. After 6 hours, filters were fixed with 4% paraformaldehyde (15 min, 4 deg C.), cells from the top surface of the filters were removed by a cotton swab, and nuclei stained with Hoescht 33342. Cells that had migrated through to the bottom surface of the filter were then counted under UV fluorescence, and confirmed by visualization with phase optics (5 fields/filter using a 10× phase objective). The average number of cells in four replicate wells was determined for each cell line in each of three independent experiments.

Fluorescent phagokinetic migration assay. Tissue culture vessels were prepared by pre-treatment with 50 µg/ml poly-D-lysine for 30 min at room temperature (RT), then coated with 1 µm diameter fluorescent microspheres (FLUO-SPHERES (carboxylate-modified, yellow-green, Molecular Probes F8815, or carboxylate-modified, blue F8814, 0.005% in Dulbecco's phosphate buffered saline (DPBS)) for 2 hours (RT), and washed three times with DPBS. For migration on various extracellular matrices, tissue culture dishes pre-coated with fibronectin, collagen IV, laminin (BIOCOAT, BD Biosciences catalog numbers 354428, 354402, 354404) were rinsed and coated with beads as above. Cells were plated onto these substrates at a density of ~4 cells/mm² in DMEM with 20% fetal bovine serum, incubated for 18-24 hours, and then fixed with 4% paraformaldehyde, 4 deg C., 15 minutes, and washed with DPBS.

Analysis of motility. Images of fluorescent cells on green microspheres were collected using a 10× phase objective, 0.3 NA, and Endow GFP filter cube. A 16 bit CCD camera (CAS-CADE 650, Roper Inc.) was used to capture images. Cleared areas generated by cells were traced, and cleared area and total fluorescence of individual cells measured using the METAMORPH imaging program. To prevent confounding results by overlapping paths and dividing cells, only areas cleared by single cells were measured and counted. To correlate cleared areas with fluorescence intensity, all images were collected using the same exposure time (25 ms), which was determined emperically to ensure that no pixels in the collected images were saturated. Confocal images were obtained on a Zeiss LSM510.

Transfections and staining. Cells were transfected with expression plasmid for EGFP using LIPOFECTAMINE 2000 following manufacturer's protocols. 18 hours after transfection, cells were plated onto microsphere coated dishes and allowed to migrate for 18-24 hours. Following migration assay, cells were permeablized with 0.3% Triton X-100 in phosphate buffered saline (PBS), and actin was visualized by staining with Alexa 546-labeled phalloidin (0.15 µM in PBS for 20 minutes, room temperature; Molecular Probes); DNA was visualized by incubation with Hoescht 33342 (1 µg/ml in PBS for 5 minutes, room temperature; Molecular Probes)

Figure 4:
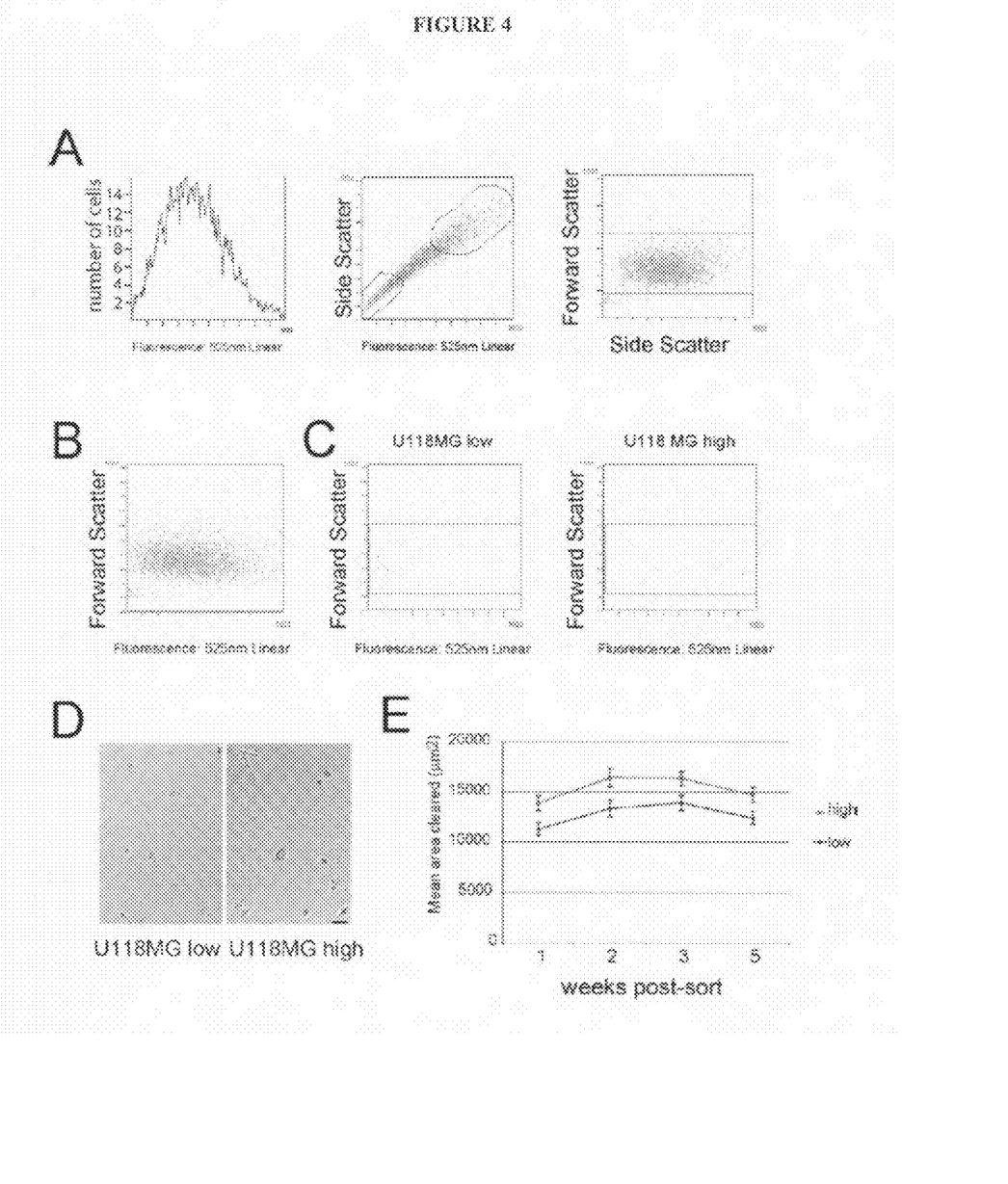

Flow cytometry. U118MG cells were plated on microsphere-coated 10 cm tissue culture dishes, incubated for 20 hours, removed using 0.25% trypsin—1 mM EDTA, and spun at 180 g for 10 minutes. Approximately $2.6\times10^5$ cells were sorted (Beckman Coulter EPICS ELITE ESP Cell Sorter) based on fluorescence intensity and side scatter characteristics. After sorting with gates arbitrarily chosen to select for approximately the top and bottom thirds of the total population by fluorescence, $4.1\times10^4$ highly fluorescent U118MG's and $2.4\times10^4$ lower fluorescence cells were recovered and returned to culture. Fluorescent signal and forward/side scatter signal is displayed on a linear scale, using 1023 available channels of resolution. Fluorescence intensity at 525 nm is displayed as typical for the flow cytometer used; there are 1023 bins into which the signal can be resolved (12 bit analog to digital converter (ADC)). An untransformed linear scale for fluorescence intensity is used. On a linear scale, the voltage measured (signal intensity) is directly proportional to the channel into which the event falls. A cell with a linear value of 100 is 10 times brighter than one in with a linear value of 10. As typical for flow cytometry, gain and threshold is set within an experiment so that the fluorescent signal is resolved into these channels. Similarly, forward and side scatter signal height is displayed in typical fashion (binned into 1023 channels). The y-axis for FIG. 4A histogram represents the number of cells in each of the histogram bins Primary astrocyte cell culture. Primary mouse cerebral cortical astrocytes were isolated from newborn mouse cortices as described (See, e.g., Segal et al., Culturing Nerve Cells 2nd edition. Edited by: G B and K G. Cambridge, Mass. London, UK, MIT Press; 1998:309-339) with the following modifications. After dissection, the cells were plated on untreated tissue culture plates at $1\times10^5$/ml in serum free DMEM with G3 glial supplement (Gibco). Cells were maintained in cultures and motility assayed within three passages.

Example 2

Migrating Cells Create Non-Fluorescent Tracks on Fluorescent Microsphere-Coated Substrates Non-cytotoxic fluorescent polystyrene microspheres have been utilized as cell labels (See, e.g., Rembaum and Dreyer, Science 1980, 208:364-368), microinjectable cell tracers (See, e.g., Wadsworth, Cell Motil Cytoskeleton 1987, 8:293-301), retrograde neuronal markers (See, e.g., Katz et al., Nature 1984, 310:498-500), and phagocytosis indicators (See, e.g., Steinkamp et al., Science 1982, 215:64-66). The phagokinetic ability of migrating cells (See, e.g., Albrecht-Buehler G, Cell 1977, 11:395-404) was taken advantage of by allowing them to ingest fluorescently labeled polystyrene microspheres coated onto a variety of migratory substrates. Tissue culture vessels prepared by pre-treatment with poly-D-lysine were coated with 1 µm diameter green fluorescent microspheres. Cells were plated onto polylysine-treated tissue culture plastic, incubated for 18-24 hours, and then fixed with 4% paraformaldehyde.

Moving cells generated microsphere-free areas in the dense fluorescent particle coat that were easily visualized using fluorescence microscopy (See FIG. 1). Differences in the motility of two glioblastoma cell lines were readily apparent by the distinctions in area of the tracks cleared (See FIG. 1B). Utilizing beads of different fluorescent emission wavelength allowed simultaneous visualization of tracks and cells stained with distinct fluorescent markers (F-actin with ALEXA FLUOR 546 Phalloidin, DNA with Hoescht 33342, or transfected with green fluorescent protein, See FIG. 1A). Confocal imaging of cells stained with ALEXA FLUOR Phalloidin migrating on microspheres reveals that ingested microspheres do not interfere with the resolution of the actin cytoskeleton (See FIG. 1D).

Figure 2:
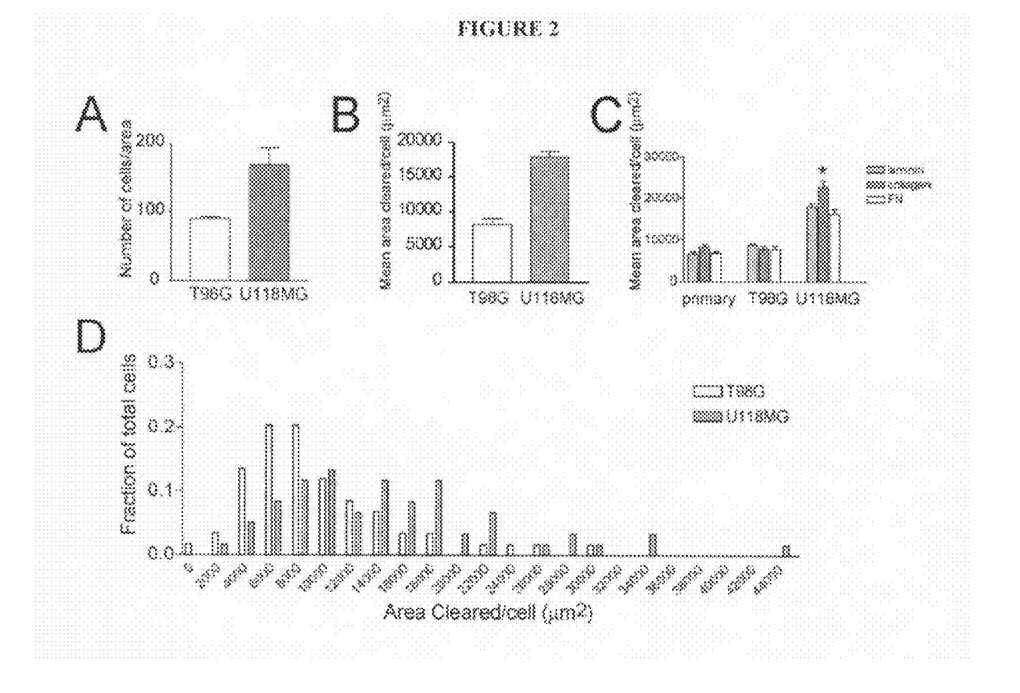

To establish a reference for comparing the motility of two glioblastoma cell lines, U118MG and T98G, a transwell filter assay was employed. Cells were seeded on the top of the membrane and allowed to migrate to a lower compartment containing media. In contrast with traditional chemotactic transwell assays, a chemoattractant gradient was not used, but instead utilized the normal growth media on both sides of the membrane (identical media used in fluorescent phagokinetic assay above). Thus, instead of chemotaxis, this assay measures pure cell motility. More (1.33 fold greater) U118MG cells were observed that had migrated through the transwell filter compared with the T98G cell line (See FIG. 2A).

To determine whether the fluorescent phagokinetic assay provided a measure of cell motility comparable to that of the transwell assay, the fluorescence-free areas cleared by single cells plated on fluorescent microspheres was measured. By tracing and measuring cleared areas generated by cells, a direct measure of how far individual cells moved in the time since plating was obtained. The area cleared per cell was obtained for at least 100 cells/cell line/independent experiment. The fluorescent phagokinetic assay showed that cells from the U118MG cell line cleared a greater mean area (2.29 fold greater) compared to the T98G cell line, an observation confirming that found with the transwell motility assay. (See FIG. 2B). Although these results suggest that comparable relative differences in intrinsic motility between cell lines are observed with these different assays, the phagokinetic assay has the advantage that an unbiased sample of cell motilities is measured. Unlike the transwell assay, in which only a small fraction of plated cells traverse the membrane (e.g., those with highest intrinsic motility), the motility measured with the fluorescent phagokinetic assay is more representative of the entire population of cells because the motility of all of the plated cells is recorded on the plate.

Interactions with local host microenvironment plays a crucial role in cancer spread, in part by regulating cell motility (See, e.g., Liotta and Kohn, Nature 2001, 411:375-379). For cell migration to occur, complex interaction between cells and the extracellular matrix regulate local adhesion and cytoskeletal rearrangements (See, e.g., Ridley et al., Science 2003, 302:1704-1709). To determine the utility of this approach to assess cell motility on different extracellular matrices, extracellular matrix substrates (e.g., laminin, fibronectin, type IV collagen) were coated with fluorescent microspheres, and differences in the motility of a variety of cell types on these substrates were determined (See FIG. 2C). To examine whether the motility of primary cells could be examined with this technique, primary mouse cerebral cortical astrocytes were isolated and plated onto the coated substrates. U118MG cells remained consistently more motile than T98G, as well as primary astrocytes on all of the substrates tested ($p<0.001$ for each pairwise comparison). The motility of U118MG cells on collagen IV was significantly greater than observed on either laminin or fibronectin ($p<0.001$). These studies confirm the applicability of analyzing population motility characteristics with the fluorescent phagokinetic assay with multiple cell types and extracellular substrates.

Example 3

Fluorescence of Individual Cells is Proportional to Motility

The ability of tumor cells to acquire greater malignancy over time is well established, and despite the monoclonal origin of most tumors, they are heterogenous at clinical presentation (See, e.g., Cotran R S: Robbins pathologic basis of disease. 6th edition. Philadelphia, Saunders; 1999:1424). Using the fluorescent phagokinetic assay, individual cell characteristics can be measured with fluorescent microscopy, making subtle differences in motility readily apparent. By measuring cell motility on a single cell level, the motility of individual cells within clonal cell lines was found to be distributed widely (See FIG. 2D). Although documentation of individual cell motility by microscopy is straightforward, analyzing large number of cells remains cumbersome, and the desire to isolate and recover cells with differing motilities led to the development of the present invention (e.g., alternatives to manual microscopic analysis).

Figure 3:
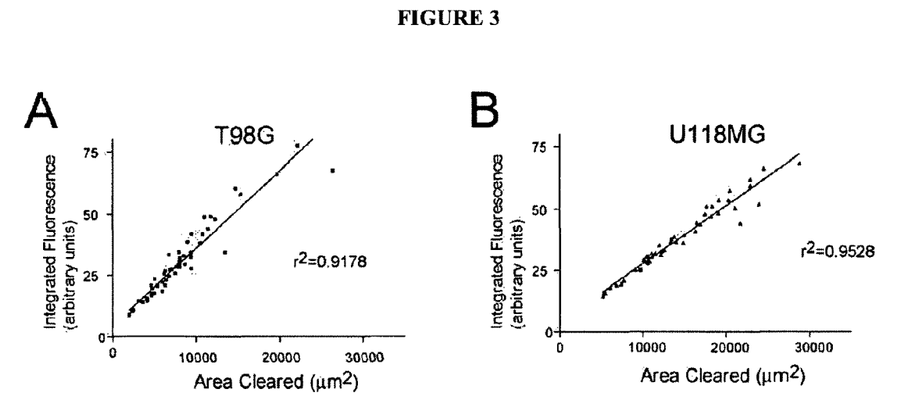

Because the area of the tracks generated by cells relates directly to the quantity of fluorescent microspheres consumed, it was reasoned that cell fluorescence could serve as another indicator of motility. By quantifying total cell fluorescence of individual cells, it was determined that single cell fluorescence was directly related to the area of fluorescence cleared (See FIG. 3; e.g., in some embodiments, the differences in slope measured result from differences in gain settings between experiments to maximally utilize the dynamic range of a CCD camera). This relationship between fluorescence and motility provides an approach by which cells of different motility can be isolated by fluorescent cell sorting. Accordingly, in some embodiments, the present invention provides a method of sorting cells of different motility by isolating cells by fluorescent sorting using a motility assay of the present invention.

Example 4

Cells with Intrinsic Motility Differences can be Sorted and Enriched by Fluorescence To isolate cells based on fluorescence, U118MG cells were plated on microsphere-coated culture dishes, allowed to migrate for 20 hours, and sorted (Beckman Coulter EPICS ELITE ESP Cell Sorter) based on fluorescence intensity and side scatter characteristics. Fluorescence (e.g., of phagocytosed spheres) correlated with side scatter (cell granularity (e.g., resulting from the microspheres)) (See FIG. 4A). Fluorescence intensity is not correlated with cell size (See FIG. 4B forward scatter (cell size) vs. fluorescence), and no morphological differences were found between high motility and low motility cells. After sorting the cells with gates arbitrarily chosen to select for approximately the top and bottom thirds of the total population by fluorescence, high fluorescence and low fluorescence U118MG cells (See FIG. 4D) were recovered and replated. A small number of sorted cells were re-characterized by flow cytometry to verify the effectiveness of the sort, and fluorescence did not correlate with cell size (forward scatter (cell size) vs. fluorescence; See FIG. 4C). When motility of post-sorted populations was determined with the fluorescent phagokinetic assay after one to five weeks in culture post-sorting, the sorted high fluorescence cells retained significantly higher motility than the low fluorescence cells (p=0.0230; See FIG. 4E). Thus, the present invention provides that intrinsic and long-term heterogeneity exists within cell lines despite their original clonal origins. In some embodiments, compositions and methods of the present invention are utilized to identify (e.g., characterize, isolate, and/or purify) cell populations (e.g., from a cell line or a sample comprising cells (e.g., a heterogeneous population of cells or cell lines).

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

I claim:

1. A method of sorting cells based on motility comprising:
    a) providing:
        i) a plurality of cells from a single cell line; and
        ii) a substrate covered with fluorescent microspheres;
    b) contacting said plurality of cells with said substrate;
    c) providing time for said cells to migrate on said substrate, wherein said cells phagocytose said fluorescent microspheres upon migration; and
    d) sorting said cells based on the fluorescence of said microspheres phagocytosed by said cells, thereby creating populations of cells with intrinsic motility differences, wherein said populations maintain said intrinsic motility differences upon culturing of said populations.

2. The method of claim 1, wherein said cells display a level of fluorescence intensity, and wherein said cells are sorted based on said fluorescence intensity.

3. The method of claim 1, wherein said cells display side scatter characteristics, and wherein said cells are sorted based on said side scatter characteristics.

4. The method of claim 2, wherein fluorescence intensity is correlated with the motility of said cells.

5. The method of claim 1, wherein said fluorescent microspheres are selected from the group consisting of polystyrene microspheres, carboxylate-modified microspheres, sulfate microspheres, aldehyde-sulfate microspheres, and amine-modified microspheres.

6. The method of claim 2, wherein cells with a greater amount of fluorescence intensity as compared to cells with a lower amount of fluorescent intensity is indicative of cells with greater motility.

7. The method of claim 1, wherein said sorted cells are cultured post said sorting said cells.

8. The method of claim 1, wherein said groups of sorted cells are characterized to determine the molecular differences between said groups.

9. The method of claim 1, wherein said microspheres are about 1 μm in diameter.

* * * * *